United States Patent [19]

Scheben et al.

[11] 3,970,697

[45] July 20, 1976

[54] OXIDATION OF ETHYLENE TO ACETIC ACID

[75] Inventors: John A. Scheben, Erlanger, Ky.; James A. Hinnenkamp; Irving L. Mador, both of Cincinnati, Ohio

[73] Assignee: National Distillers and Chemical Corporation, New York, N.Y.

[22] Filed: July 1, 1974

[21] Appl. No.: 485,046

[52] U.S. Cl. .................. 260/533 R; 260/604 AC
[51] Int. Cl.² ..................................... C07C 51/32
[58] Field of Search ............................ 260/533 R

[56] References Cited
UNITED STATES PATENTS

| | | | |
|---|---|---|---|
| 2,900,412 | 8/1959 | Toland | 260/533 R X |
| 2,903,480 | 9/1959 | Toland | 260/533 R X |
| 3,240,805 | 3/1966 | Naglieri | 260/533 R |
| 3,534,093 | 10/1970 | Gerberich | 260/533 R |
| 3,792,087 | 2/1974 | McClain | 260/533 R |
| 3,806,544 | 4/1974 | Suzuki | 260/533 R |

FOREIGN PATENTS OR APPLICATIONS

| | | | |
|---|---|---|---|
| 46-6,763 | 2/1971 | Japan | 260/533 R |

*Primary Examiner*—Vivian Garner
*Attorney, Agent, or Firm*—Kenneth D. Tremain

[57] ABSTRACT

A process for the selective production of acetic acid from ethylene with co-production in minor amounts of carbon oxides, by reaction of ethylene and oxygen in the presence of water and a catalyst composition contaning a catalytically effective amount of palladium metal and a sulfur modifier.

13 Claims, No Drawings

OXIDATION OF ETHYLENE TO ACETIC ACID

BACKGROUND OF THE INVENTION

The vapor phase oxidation of ethylene to acetaldehyde is well known. For example, in the Wacker process, as illustrated by U.S. Pat. No. 3,131,223, ethylene together with an oxygen containing gas and water vapor are passed over a noble metal compound catalyst to produce the aldehyde. The use of redox components to maintain the noble metal catalyst constituent in the oxidized state (U.S. Pat. No. 3,131,223; 3,057,915; and 3,301,905), with acids, e.g., sulfuric acid, nitric acid, hydrochloric acid, phosphoric acid or acetic acid, to increase anion concentrations (U.S. Pat. No. 3,131,223 or 3,057,915) has been described as increasing catalytic activity in such operations. The use of a noble metal catalyst is disclosed in U.S. Pat. No. 3,439,044. In all of the above processes, however, the principal reaction product formed is acetaldehyde, at most only small amounts of acetic acid being produced as a by-product in the reaction.

U.S. Pat. No. 3,534,093 discloses a process for the preparation of acetaldehyde, acetic acid and acetic anhydride by the oxidation of ethylene in the presence of a palladium metal or palladium-gold alloy catalyst.

Commercial techniques for the manufacture of acetic acid from ethylene have involved hydrating the olefin to ethanol followed by dehydrogenation and oxidatively dehydrogenating the ethanol to acetaldehyde and then oxidizing the acetaldehyde to acetic acid, or initially oxidizing the ethylene to acetaldehyde followed by a second oxidation under different conditions to obtain the acetic acid.

A one-step vapor phase process for the oxidation of ethylene, in the presence of a catalyst containing palladium chloride and a vanadium or molybdenum oxide, is described in U.S. Pat. No. 3,240,805. The use of a combination catalyst comprising a noble metal compound, a compound of a transition metal of Groups I, VII and VIII, an alkali metal compound and a compound of a transition metal element of Groups III-VI for such purpose is taught in U.S. Pat. No. 3,293,291. A further variation using a catalyst mixture of a salt or coordination compound of palladium and a carboxylate of iron, cobalt or manganese is disclosed in U.S. Pat. No. 3,459,796. British Pat. No. 1,142,897 suggests employing yet another catalyst system, viz, a support mixture of palladium metal and a transition metal oxide or salt, for the ethylene base production of acetic acid. In general, however, commercial adoption of these procedures has not been possible because of the relatively large amounts of by-product acetaldehyde simultaneously produced therein and/or the concomitant large losses of ethylene reactant attributable to combustion to carbon dioxide.

Reyerson and Swearingen, J. Am. Chem. Soc. 50, 2872, observed that ethylene is effectively oxidized to carbon dioxide and water at 100° C. in the presence of supported palladium or platinum catalysts. Our work has confirmed these observations and has also shown that the same products are obtained without regard to the nature of the support.

U.S. patent application Ser. No. 197,528, now U.S. Pat. No. 3,792,087, discloses a vapor phase process for oxidizing ethylene to acetic acid with oxygen in the process of palladium metal supported on a carrier and impregnated with phosphoric acid. Phosphoric acid is apparently unique, since other phosphates, pyrophosphates, organic phosphorus compounds, etc., likely do not function in this oxidation system.

In order to achieve the selective oxidation of ethylene in the presence of a noble metal catalyst, one must first control the complete oxidation reaction, and then selectively initiate the partial oxidation. We have now found that certain sulfur compounds will moderate noble metal catalysts so as to yield selective oxidation catalysts and these catalysts can be used in either the vapor phase, liquid phase or trickle phase reaction systems.

It is accordingly a principal object of the present invention to provide a process for the selective preparation of acetic acid by the oxidation of ethylene with attendant low production of combustibles and acetaldehyde. Further objects and advantages of the invention will become apparent to those skilled in the art from the following detailed description of the preferred forms thereof.

SUMMARY OF THE INVENTION

It has been found that acetic acid is selectively produced when ethylene is oxidized in the presence of a catalyst composition containing a catalytically effective amount of a palladium metal and certain sulfur modifiers. The process is carried out at elevated temperatures employing a heterogeneous catalyst contact system, e.g., systems utilizing fixed, moving or fluidized catalyst beds. The catalysts can be used in vapor phase and liquid phase systems and also in mixed vapor-liquid phase systems which are sometimes called trickle phase or dropping phase systems.

PREFERRED EMBODIMENTS OF THE INVENTION

In accordance with this invention, a reactant feed comprising ethylene, oxygen and water is contacted with a catalyst to selectively form acetic acid by the following overall reaction (the specific mechanism of which is not, however, completely understood):

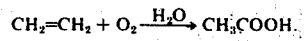

The vapor phase reaction is carried out by passing a gaseous reaction mixture of ethylene, oxygen and water, with or without further diluents, into contact with the catalyst. The gaseous mixture may be contacted with the catalyst in any suitable manner, whether by maintaining the latter in a fixed or moving bed or by utilizing fluidized bed operations.

The vapor phase reaction is suitably carried out at temperatures within the range of from about 100°–250° C., preferably up to about 220° C. Temperatures greater than about the latter value may result in undue ethylene combustion and increase side reactions, e.g., ethylene polymerization. Either atmospheric or elevated pressures can be used, the use of higher pressures somewhat increasing product conversions. The reaction can thus be effected at pressures of up to about 20 atmospheres. It is, however, generally preferred to carry out the vapor phase process under pressures only slighly in excess of atmospheric, e.g., up to about 10 atmospheres, to increase productivity and catalyst efficiency.

The liquid phase reaction is suitably carried out at temperatures within the range of about 60°–220° C., and preferably about 90°–200° C. Elevated pressure is usually necessary in order to maintain the reactants in the liquid phase and the pressure can be up to about 100 atmospheres. It is generally preferred to carry out the liquid phase process under pressures of up to 80 atmospheres.

The ethylene may be employed in the pure form or can be impure in the sense that it may contain as an inert diluent, minor amounts, e.g., up to about 50 mol percent thereof, incorporated in the feed mixture, of a saturated hydrocarbon such as methane, ethane or propane. The oxygen in the feed can similarly be pure oxygen or an oxygen containing gas mixture such as air or air enriched with oxygen. In addition to these materials, the feed mixture reacted in the process of this invention can contain other inert diluents such as carbon dioxide, nitrogen or acetic acid. Acetic acid can replace a portion of the water feed in the vapor phase process, whereby reducing process heat loads in recycle operations.

While stoichiometric proportions of the ethylene and oxygen reactants, viz, equimolar proportions thereof, can be utilized in the process of this invention, such compositions are normally within the flammability range. It is therefore preferred to operate with an oxygen lean feed, i.e., where the oxygen is the limiting reactant present. Such a feed can contain about 5–20 moles percent oxygen. The addition of acetic acid to the feed as an inert diluent is particularly effective in extending the flammability limit for oxygen lean feeds.

The equation for formation of acetic acid does not require water as a reactant. In practice, however, it has been found that high conversions and selectivities to acetic acid are obtained when the feed does contain water. The water also serves to remove some of the heat of reaction. In the vapor phase reaction, the relative amount of water can range from about 0.2–10, preferably about 1–8 moles per mole of oxygen. In the liquid phase system, water or aqueous acetic acid is employed as the reaction medium and the molar ratio of water to oxygen can be substantially higher, e.g., up to 100 moles per mole of oxygen.

As indicated hereinabove, the reaction mixture is contacted with a supported catalyst composition incorporating a catalytically effective amount of palladium metal and a sulfur modifier. Carriers conveniently employed in the catalyst art including, for example, silica, alumina, silica-alumina, carbon such as activated carbon or the like, titania, zirconia or glass beads, can be employed as such supported catalyst materials. The supports are impregnated or loaded with the sulfur modifiers and the palladium metal, whether alone or admixed, alloyed, or in solid solution with a further metal (e.g., a material selected from Groups IB or VIII of the Periodic Table of the Elements appearing on pages 60–61 of Lange's Handbook of Chemistry (Revised 10th Edition), is deposited on the support The catalytically effective palladium metal and sulfur modifier can be deposited on or impregnated in the catalyst carrier in any desired manner or sequence, the combined supported catalyst composition, however, formed, being active in the processes of this invention.

The palladium metal is incorporated in amounts of from about 0.01–6%, preferably from about 0.1–5% by weight of the supported catalyst composition. We prefer to use a combined palladium-gold catalyst since the gold improves the catalyst stability and promotes activity. The gold content can be about 0.01–5%, preferably about 0.1–3%, by weight of the supported catalyst composition. The weight ratio of palladium to gold can vary between about 1:3–3:1 and is preferably about 2:1.

Deposition of the catalytic metals on the support is effected by conventional techniques.

We have found that certain sulfur containing modifiers show utility in modifying the noble metal catalyst in a manner to promote the oxidation of ethylene to acetic acid and to prevent the complete oxidation of ethylene to carbon oxides and water. The modifiers found applicable include sulfur dioxide, sulfur trioxide, sulfuric acid, sulfurous acid, trifluoromethanesulfonic acid, p-toluenesulfonic acid, potassium acid sulfate, magnesium sulfate, and aluminum potassium sulfate.

The sulfur modifiers used in this invention must have at least two atoms of oxygen, and can have three to four atoms of oxygen, associated with each sulfur atom. The modifiers are thus either oxides or inorganic and organic acids and the salts thereof. The oxides are $SO_2$ and $SO_3$, and the inorganic acids are sulfurous acid and sulfuric acid. The organic acids are sulfonic acids containing a sulfur attached to a carbon atom, e.g., B-naphthalene sulfonic acid, dodecanesulfonic acid and 1,3,6-naphthalene sulfonic acid. Applicable salts of inorganic and organic acids include Group I through Group IV metal and transition metal salts such as sodium benzene sulfonate, cobalt sulfate and potassium sulfite.

The concentration of the sulfur compound can range from about 0.05–25%, preferably about 0.1–15%, by weight of the supported catalyst composition. The concentration of the sulfur compound will change with nature of the support and the sulfur compound itself. For example, carbon supported catalysts absorb fairly large amounts of gaseous $SO_2$ even at 25° C. (from 0.8–7%). Silica and alumina supported catalysts absorb less sulfur dioxide at this temperature (on the order of about 0.05–2%). Thus, it is convenient to treat these catalysts with gaseous sulfur dioxide at temperatures greater than 25°C. Preferably, the treating temperature is in a range of 25°–300° C. Gaseous sulfur dioxide can be fed over the catalyst at the desired temperature either in the pure state or diluted with air or nitrogen. An active catalyst can also be prepared by passing moist air and sulfur dioxide gas over these catalysts within the foregoing temperature range. Aqueous solutions of $SO_2$ can be prepared by saturating water at various temperatures with gaseous $SO_2$ and the resulting sulfurous acid solutions can be used to impregnate the catalyst.

Sulfur trioxide is a liquid at room temperature. It is convenient to modify the catalyst with $SO_3$ by passing its vapors over the catalyst at 25°–200° C. An inert gas such as nitrogen, argon or helium, serves to carry the $SO_3$ vapors over the catalyst.

Sulfuric acid, trifluoromethanesulfonic acid, p-toluenesulfonic acid, potassium acid sulfate, cobalt sulfate, manganese sulfate, and aluminium potassium sulfate, are added to the catalyst by impregnating with aqueous solutions of the desired sulfur modifier. The catalyst is then dried before use.

It will be recognized by those skilled in the art that additional quantities of the sulfur modifiers can be added to the reaction zone continuously or intermittently during the course of the reaction. As just one example, the sulfurous acid solutions can be incorporated into water being fed to the reaction zone.

The following Examples are set forth in order to further illustrate the invention but are not intended to limit it. Throughout this specification and claims, all parts and percentages are by weight and all temperatures are in degree centigrade unless otherwise specified. Further, as employed herein, the "selectivity" of a product's formation is defined as follows:

$$\% \text{ Selectivity} = \frac{\text{Moles of product formed}}{\text{Moles of specified reactant reacted.}}$$

CATALYST PREPARATION

EXAMPLE 1

60 g of a catalyst composed of 1.3% palladium and 0.6% by weight gold on a carbon support was placed in a glass tube. Gaseous sulfur dioxide was passed through the catalyst at ambient temperature at the rate of 11 ml/min. Within a short time the temperature in the catalyst bed rose from 26° to 75° C. due to the heat of absorption. The gas feed was continued for 1 hour and then the sample was evacuated at 18 mm pressure and 55° C. for 1 hour in a rotary film evaporator. The increase in catalyst weight was 1.14 g.

EXAMPLE 2

60.49 g of a catalyst containing 1.3% palladium and 2.6% gold deposited on a silica carrier was placed in an upright glass tube mounted in a furnace and $SO_2$ vapors along with moist air (air saturated with water at ambient temperature) were passed over the catalyst while heating to 200° C. This temperature was maintained for 30 minutes under the sulfur dioxide-moist air feeds (total flow 6 ml/min of 1:1 $SO_2$: air mixture). The increase in catalyst weight was 2.66 g.

EXAMPLE 3

Vapors of sulfur dioxide and moist air (air containing 2–3% by volume of water) were passed over 9.4 g of 0.6% palladium and 0.6% gold on silica-alumina catalyst while heating to 200° C. The temperature was held at 200° C. for 30 minutes under the sulfur dioxide-moist air feeds. Then, the treated catalyst was cooled under dry air. The increase in catalyst weight was 0.11 g.

EXAMPLE 4

Nitrogen gas was passed through a saturator containing liquid sulfur trioxide at ambient temperature. The nitrogen diluted sulfur trioxide vapors then passed through 9.8 g of 1.3% palladium and 0.6% gold on carbon catalyst mounted in a glass tube. This treatment was continued for 30 minutes during which time the temperature increased to 65° C. Then the system was purged with nitrogen for 15 minutes and the sample evacuated at 18 mm pressure and 55° C. for 90 minutes. The increase in catalyst weight was 1.46 g.

EXAMPLE 5

An aqueous solution of $KHSO_4$ (0.25 g/10 ml) was added to 6 g of a catalyst containing 1.3% palladium and 0.6% gold on a silica carrier. The mixture was concentrated under reduced pressure at 55° C. and finally the modifier catalyst was vacuum dried at 1 mm pressure and 60° C. This catalyst contained 4% $KHSO_4$ by weight.

EXAMPLE 6

5 g of silica base catalyst was placed in a 125 ml flat bottom baffled flask. To this was added 8.8 ml of an aqueous solution containing 0.018 g of 95% sulfuric acid. The mixture was concentrated and vacuum dried. The silica base catalyst contained 1.3% palladium, 0.6% gold and 0.35% sulfuric acid based on the total sample weight.

VAPOR PHASE ETHYLENE OXIDATION

General Experimental Procedure 12 ml of the sulfur modified catalyst was placed in a 5/8 inch O.D. × 11 inches long stainless steel reactor fitted with a thermowell in the catalyst bed and an inlet and outlet. The reactor was heated by an electrically wrapped brass annular block. Temperatures were maintained by a controlling pyrometer. The reaction temperatures cited were those found in the catalyst bed.

Ethylene and oxygen in the molar feed ratio of 1:1 to 10:1 were fed from calibrated rotameters. Water was fed from a syringe type pump with continuous drive. The combined feeds, i.e., ethylene, oxygen and water, were conducted through a preheater section mounted on top of the reactor section. Temperatures in the preheater were the same as those in the reactor. The desired system pressure was maintained by a back pressure let-down valve. By changing the total moles of reactants fed, the contact time was varied from 3 to 36 seconds.

Immediately after the let-down valve, the exit gases were sequentially chilled in wet ice and dry ice-isopropanol baths to trap out the condensable products. These products were analyzed for acetic acid and acetaldehyde. The non-condensables were analyzed to determine the amount of oxygen vented and the concentration of combustion products.

EXAMPLE 7

6.26 g (12 ml) of catalyst composed of 1.3% palladium, 0.6% gold and 4% sulfur dioxide deposited on 12 × 30 mesh carbon carrier, 1150 m²/g surface area, was placed in the reactor and heated to about 120° C. Ethylene (4.98 l/hr), oxygen (0.97 l/hr) and water (3.14 ml/hr) feeds were combined immediately prior to the preheater. The vapors were then introduced into the reactor. Because of the heat of reaction liberated, the actual temperature of the catalyst was about 150° C. The molar feed ratio of 5:1:4, $C_2H_4$:$O_2$:$H_2O$ was maintained at 75 psig.

After allowing a 2 hour equilibrium period, a 1 hour sample was taken and analyzed. The acetic acid production amounted to 14 g per gram of palladium. Oxygen conversion was 78%, and the ethylene selectivity to acetic acid 74%. In addition, 10% of the ethylene reacted was converted to acetaldehyde and 16% was burned to carbon dioxide.

This sampling was continued on a scheduled basis in order to follow the catalyst activity and stability. After 100 hours of operation, the acetic acid production was 13.5 g per gram of palladium per hour. The conversion of the oxygen fed amounted to 60%. Acetic acid selectivity on ethylene was 85%, 2% to acetaldehyde and 13% to combustion products.

EXAMPLE 8

This Example demonstrates the influence of temperature, pressure and molar feed ratios. A 1.3% palladium, 0.6% gold, 0.14% $SO_2$ on silica, 1/8 inch × 1/8 inch extruded, 100 $m^2$/g surface area, catalyst (4.16 g,

| Ex. No. | Catalyst | Catalyst Wt. grams | Reaction Temp. °C | Reaction Pressure psig | Hourly g. HOAc g. Pd | % Conversion Oxygen | % Selectivity HOAC | % Selectivity HAc | % Selectivity $CO_2$ |
|---|---|---|---|---|---|---|---|---|---|
| 9 | 1.3% Pd, 0.6% Au on Silica | 4.2 | 150 | 50 | 0 | 94 | 0 | 0 | 100 |
| 10 | 1.6% $SO_2$ on Silica | 4.4 | 150 | 50 | 0 | 0 | 0 | 0 | 0 |
| 11 | 1.3% Pd, 0.6% Au, 3.7% $SO_2$ on Carbon | 6.2 | 150 | 50 | 16 | 70 | 85 | 5 | 10 |
| 12 | 1% Pd, 1% $SO_2$ on Carbon | 6.3 | 150 | 75 | 4 | 24 | 53 | 20 | 27 |
| 13 | 0.4% Pd, 0.8% Au, 1.1% $SO_2$ on Silica | 4.0 | 150 | 75 | 44 | 29 | 80 | 14 | 6 |
| 14 | 0.5% Pd, 3.7% $SO_2$ on Silica-Alumina | 6.2 | 170 | 75 | 4 | 44 | 24 | 0 | 76 |
| 15 | 3% Pd, 1.2% Au, 2.3% $SO_2$ on Carbon | 6.5 | 150 | 50 | 6 | 100 | 62 | 9 | 29 |
| 16 | 1.2% Pd, 0.6% Au, 0.4% $H_2SO_4$, 4% $SO_2$ on Carbon | 6.3 | 170 | 75 | 15 | 80 | 78 | 0 | 22 |
| 17 | 1.1% Pd, 0.5% Au, 12% $SO_3$ on Silica | 4.5 | 150 | 75 | 10 | 38 | 59 | 27 | 14 |
| 18 | 1.1% Pd, 0.5% Au, 13% $SO_3$ on Carbon | 9.3 | 170 | 100 | 16 | 65 | 76 | 10 | 14 |
| 19 | 1.3% Pd, 0.6% Au, 4% $KHSO_4$ on Silica | 4.0 | 170 | 75 | 11 | 39 | 70 | 5 | 25 |
| 20 | 1.2% Pd, 0.6% Au, 8% $KHSO_4$ on Carbon | 6.0 | 150 | 75 | 8 | 44 | 69 | 0 | 31 |
| 21 | 1.3% Pd, 0.6% Au, 4% $MnSO_4$ on Carbon | 6.1 | 150 | 75 | 9 | 39 | 82 | 3 | 15 |
| 22 | 1.3% Pd, 0.6% Au, 2% $AlK(SO_4)_2$ on Silica | 4.1 | 150 | 75 | 4 | 22 | 59 | 5 | 36 |
| 23 | 1.3% Pd, 0.6% Au, 0.4% $H_2SO_4$ on Silica | 4.2 | 150 | 50 | 12 | 36 | 83 | 8 | 9 |
| 24 | 1.2% Pd, 0.5% Au, 10% $CF_3SO_3H$ on $Al_2O_3$ | 13.8 | 150 | 50 | 10 | 100 | 79 | 0 | 21 |
| 25 | 0.5% Pd, 3.3% $SO_2$ on Titania | 10.5 | 160 | 100 | 17 | 33 | 82 | 6 | 12 |
| 26 | 1.3% Pd, 0.6% Au, 1.8% $SO_2$ on Zirconia | 14.5 | 150 | 75 | 6 | 68 | 64 | 22 | 14 |

12 ml) was employed. The contact time varied between 10 and 20 seconds.

| Reaction Temp. °C. | Reaction Pressure psig | Molar Feed Ratio $C_2H_4$:$O_2$:$H_2O$ | | | Hourly g HOAc g Pd | % Conversion $O_2$ | % Selectivity HOAC | % Selectivity HAc | % Selectivity $CO_2$ |
|---|---|---|---|---|---|---|---|---|---|
| 150 | 50 | 5 | 1 | 4 | 14 | 39 | 78 | 14 | 8 |
| 155 | 75 | 5 | 1 | 4 | 20 | 57 | 79 | 10 | 11 |
| 160 | 75 | 5 | 1 | 4 | 25 | 65 | 83 | 9 | 8 |
| 165 | 75 | 5 | 1 | 4 | 24 | 62 | 82 | 9 | 9 |
| 165 | 75 | 4 | 1 | 5 | 20 | 58 | 78 | 9 | 12 |
| 170 | 75 | 4 | 1 | 5 | 21 | 64 | 78 | 8 | 14 |
| 170 | 75 | 3 | 1 | 6 | 16 | 48 | 74 | 13 | 13 |

HOAc — Acetic acid
HAc — Acetaldehyde

EXAMPLES 9–26

These Examples further demonstrate the utility of the sulfur modified catalysts and confirm the particulars set out in the specification. In summary,

| Example | |
|---|---|
| 9 | Shows complete combustion in the presence of Pd + Au/silica catalyst. |
| 10 | Confirms that no products are formed with $SO_2$ only. |
| 11 | Demonstrates the activity of $SO_2$ modified Pd + Au/carbon catalyst. |
| 12 | Shows the activity of a Pd catalyst modified with $SO_2$. |
| 13 | Low metals loading. |
| 14 | Silica-alumina support with Pd and $SO_2$ |
| 15 | High metals loading. |
| 16 | Combination of $H_2SO_4$ and $SO_2$ modifiers. |
| 17 | Silica catalyst modified with $SO_3$. |
| 18 | Carbon catalyst modified with $SO_3$. |
| 19 | Silica catalyst modified with $KHSO_4$. |
| 20 | Carbon catalyst modified with $KHSO_4$. |
| 21 | $MnSO_4$ modifier. |
| 22 | $AlK(SO_4)_2$ modifier. |
| 23 | $H_2SO_4$ modifier. |
| 24 | $CF_3SO_3H$ modifier. |
| 25 | Titania support with Pd and $SO_2$. |
| 26 | Zirconia support with Pd, Au and $SO_2$. | ethylene:oxygen:water.

In each of these Examples, the molar feed ratio was 5:1:4 of ethylene-oxygen-water. HOAc in the following Table designates acetic acid and HAc signifies acetaldehyde.

LIQUID PHASE ETHYLENE OXIDATION

These preparations were performed in a 70 ml stainless steel reactor. The procedure was to add the palladium supported catalyst and reaction medium to the reactor. The system was closed and pressurized with ethylene and air to the desired pressure, 5–100 atmospheres. The reactor was then heated and shaken for the prescribed time (60° to 200° C. for 0.5 to 5 hours).

At the end of the reaction period, the reactor contents were chilled in wet ice and the vent gases analyzed to determine the oxygen remaining and the amount of combustion products. The liquid products were filtered to remove the catalyst and then analyzed for acetic acid, acetaldehyde and other oxygenated products.

The following Examples further exemplify this procedure.

EXAMPLE 27

To the reactor was added 0.98 g (0.46m moles Pd) of 5% palladium on carbon catalyst, 10 ml (0.5 mole) of deionized water, 0.048 g (0.46m moles) 98% sulfuric acid. After closing the reactor, ethylene was added to 27 atmospheres pressure, then air to 55 atmospheres total pressure. Molar ratio $C_2H_4$:$O_2$:$H_2O$:$N_2$ = 5:1:44:4. The reactor contents were heated at 100° C. for 1 hour with shaking.

Analysis of the reaction products and vent gases showed an acetic acid production of 5 m moles or 6 g of acetic acid per gram of palladium per hour. The oxygen conversion was 94% with 80% selectivity of the ethylene to acetic acid.

EXAMPLE 28

With p-toluenesulfonic acid 1.6 g (9.5 m moles substituted for sulfuric acid in Example 27, an hourly acetic acid production of 3.7 m moles or 4.4 g per gram of palladium was found. Ethylene selectivity values were 56% to acetic acid, 29% to acetaldehyde and 15% to carbon dioxide.

EXAMPLE 29

When trifluoromethanesulfonic acid (9m moles) was employed as the sulfur modifier in Example 27, 5m moles of acetic acid was formed per hour. At 97% oxygen conversion, the acetic acid selectively based on ethylene amounted to 61%. In addition, some of the ethylene was oxidized to acetaldehyde (25%), and some to carbon dioxide (13%).

The Examples above illustrate the use of catalyst systems containing nominal amounts of certain modifiers. While comparable results have been attained with phosphoric acid modified catalysts (U.S. patent application Ser. No. 197,528, now U.S. Pat. No. 3,792,087) the latter requires the use of substantially larger amounts of phosphoric acid, which are inherently difficult to handle. The differences in modifier usage are illustrated by the following comparison, wherein all of the experimental conditions were identical.

| Example | Catalyst | Modifier | Hourly g.HOAc/g. Pd |
|---------|----------|----------|---------------------|
| A | 1.3% Pd, 0.6% Au on SiO$_2$ | 0.4% H$_2$SO$_4$ | 11.9 |
| B | 1.3% Pd, 0.6% Au on SiO$_2$ | 0.7% SO$_2$ | 12.0 |
| C | 1.0% Pd, 0.5% Au on SiO$_2$ | 25 % H$_3$PO$_4$ | 11.9 |
| D | 1.3% Pd, 0.6% Au on SiO$_2$ | 0.4% H$_3$PO$_4$ | 0.87 |

Examples A and B exemplify the small amount of modifier that can be effective in the present invention. In Example C comparable results are obtained by using phosphoric acid, but in substantial amount. Example D shows that phosphoric acid in amount similar to the sulfur modifiers of A and B is unsatisfactory.

From the preceding, it will be apparent that the present invention provides an improved process for the selective formation of acetic acid by the oxidation of ethylene. Since various changes and modifications may be made in the preferred embodiment of the process described hereinabove without departing from the spirit and scope of the invention, it is intended that the preceding description should be construed as illustrative and not in a limiting sense.

We claim:

1. In a process for the selective production of acetic acid by reacting ethylene and oxygen with added water in the feed over a supported catalyst consisting essentially of palladium metal or palladium metal and gold metal in a catalytically effective amount, the improvement which comprises conducting the process in the presence of a sulfur-containing catalyst modifier having 2-4 atoms of oxygen per sulfur atom wherein the sulfur modifier is sulfur dioxide, sulfur trioxide, sulfurous acid, sulfuric acid, a sulfonic acid, or a salt of said acids and said sulfur modifier is impregnated in the catalyst support in an amount of about 0.05-25% by weight of the supported catalyst.

2. The process of claim 1 wherein said sulfur modifier is selected from the group consisting of sodium benzene sulfate, cobalt sulfate, potassium sulfate, trifluoromethanesulfonic acid, p-toluenesulfonic acid, potassium acid sulfate, manganese sulfate, and aluminum potassium sulfate.

3. The process of claim 1 wherein said catalytically effective amount of palladium metal is about 0.01-6% by weight of the supported catalyst.

4. The process of claim 3 wherein the palladium metal is about 0.1-5 weight percent and the amount of the sulfur modifier is about 0.1-15 weight percent.

5. The process of claim 1 wherein said supported catalyst contains gold metal in an amount of about 0.01-5 weight percent of the supported catalyst.

6. The process of claim 5 wherein said gold metal is in an amount of 0.1-3% by weight.

7. The process of claim 1 wherein said reaction is effected at an elevated temperature within the range of from about 60°-250° C. and at a pressure of from about 1-100 atmospheres.

8. The process of claim 7 wherein said reaction temperature is about 60°-220° C.

9. The process of claim 1 wherein said reaction is effected in the vapor phase.

10. The process of claim 9 wherein said mixture of ethylene, oxygen and water contains from 5-20 mole percent of oxygen and from 0.2-10 moles of water vapor per mole oxygen.

11. The process of claim 1 wherein said reaction is effected in the liquid phase.

12. The process of claim 1 wherein the reaction temperature is about 60°-220° C., the reaction pressure is about 1-100 atmospheres, the mixture of ethylene, oxygen and water contains from 5-20 mole percent of oxygen and from 0.2-100 moles of water per mole oxygen, the amount of palladium metal is about .01-6 weight percent of the supported catalyst and the catalyst contains gold metal in an amount of about 0.01-5 weight percent of the supported catalyst.

13. The process of claim 12 wherein the amount of sulfur modifier is about 0.1-15 weight percent of the supported catalyst, the amount of palladium metal is about 0.1-5 weight percent of the supported catalyst and the amount of gold is about 0.1-3 weight percent of the supported catalyst.

* * * * *